(12) United States Patent
Omata (10) Patent No.: US 6,842,501 B2
(45) Date of Patent: Jan. 11, 2005

(54) SUBSTANCE HARDNESS MEASURING INSTRUMENT, BIOLOGICAL TISSUE HARDNESS MEASURING INSTRUMENT, AND RECORDING MEDIUM FOR OUTPUTTING HARDNESS DATA ON SUBSTANCE WHEN DATA IS INPUTTED TO IT

(75) Inventor: Sadao Omata, Koriyama (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/471,978

(22) PCT Filed: Apr. 18, 2002

(86) PCT No.: PCT/JP02/03880

§ 371 (c)(1),
(2), (4) Date: Sep. 16, 2003

(87) PCT Pub. No.: WO02/085213

PCT Pub. Date: Oct. 31, 2002

(65) Prior Publication Data

US 2004/0114715 A1 Jun. 17, 2004

(30) Foreign Application Priority Data

Apr. 18, 2001 (JP) ........................................ 2001-119991

(51) Int. Cl.[7] .............................................. G01N 23/06
(52) U.S. Cl. ............................................. 378/51; 378/4
(58) Field of Search .................................. 378/4–20, 51

(56) References Cited

U.S. PATENT DOCUMENTS 5,766,137 A * 6/1998 Omata ........................ 600/587

FOREIGN PATENT DOCUMENTS

| JP | A 4-332537 | 11/1992 |
|----|------------|---------|
| JP | A 7-327971 | 12/1995 |
| JP | A 8-215183 | 8/1996 |
| JP | A 9-84769 | 3/1997 |
| JP | A 9-122107 | 5/1997 |
| JP | A 11-128181 | 5/1999 |
| JP | A 11-155852 | 6/1999 |
| JP | A 11-276468 | 10/1999 |
| JP | A 11-278967 | 10/1999 |
| JP | A 2001-430 | 1/2001 |
| JP | A 2001-29343 | 2/2001 |

OTHER PUBLICATIONS

Omata, "Measurements of the Hardness of a Soft Material with a Piezoelectric Vibrometer and Their Analysis", Medical Electronics and Bioengineering, vol. 28 No. 1, 1990, pp 1–8.

Omata et al., "New tactile sensor like the human hand and its applications", Sensors and Actuators A, 35 (1992), pp 9–15.

* cited by examiner

Primary Examiner—Craig E. Church
Assistant Examiner—Jurie Yun
(74) Attorney, Agent, or Firm—Oliff & Berridge, PLC (57) ABSTRACT

An apparatus for measuring hardness of a material that makes it possible to measure hardness of a material having high spatial resolution over a wide area, hardness of tissue of a living body, hardness of micro areas in the entire organ and express the flexibility and robustness of the tissue of the living body based on CT values of an X-ray CT scanner. It includes an X-ray scanning section that scans and irradiates a specimen with X-rays, a CT value output section that calculates and outputs a CT value by measuring intensity of X-rays that have passed through the specimen, a storage apparatus that stores the correspondence relationship between CT value data and hardness data of a plurality of reference portions of tissue of the living body, a hardness conversion operation apparatus that converts to hardness using the correspondence relationship and a display that outputs the converted hardness.

7 Claims, 6 Drawing Sheets

SUBSTANCE HARDNESS MEASURING INSTRUMENT, BIOLOGICAL TISSUE HARDNESS MEASURING INSTRUMENT, AND RECORDING MEDIUM FOR OUTPUTTING HARDNESS DATA ON SUBSTANCE WHEN DATA IS INPUTTED TO IT

TECHNICAL FIELD

The present invention relates to an apparatus for measuring the hardness of a material in relation to CT values of an X-ray CT scanner, and more particularly, to an apparatus for measuring the hardness of tissue materials of a living body, such as an organ, the hardness of micro areas of the organ, and a recording medium capable of outputting the hardness data of the material.

BACKGROUND ART

To understand the background of the present invention, it is necessary to explain two conventional technologies in different technological fields. One belongs to a technological field of apparatuses for measuring the hardness of a tissue material of a living body using a mechanical/electrical vibration system and the other belongs to a technological field concerning CT values of a tissue material of a living body using an X-ray CT scanner. The former will be explained first and then the latter will be explained.

Figure 3:
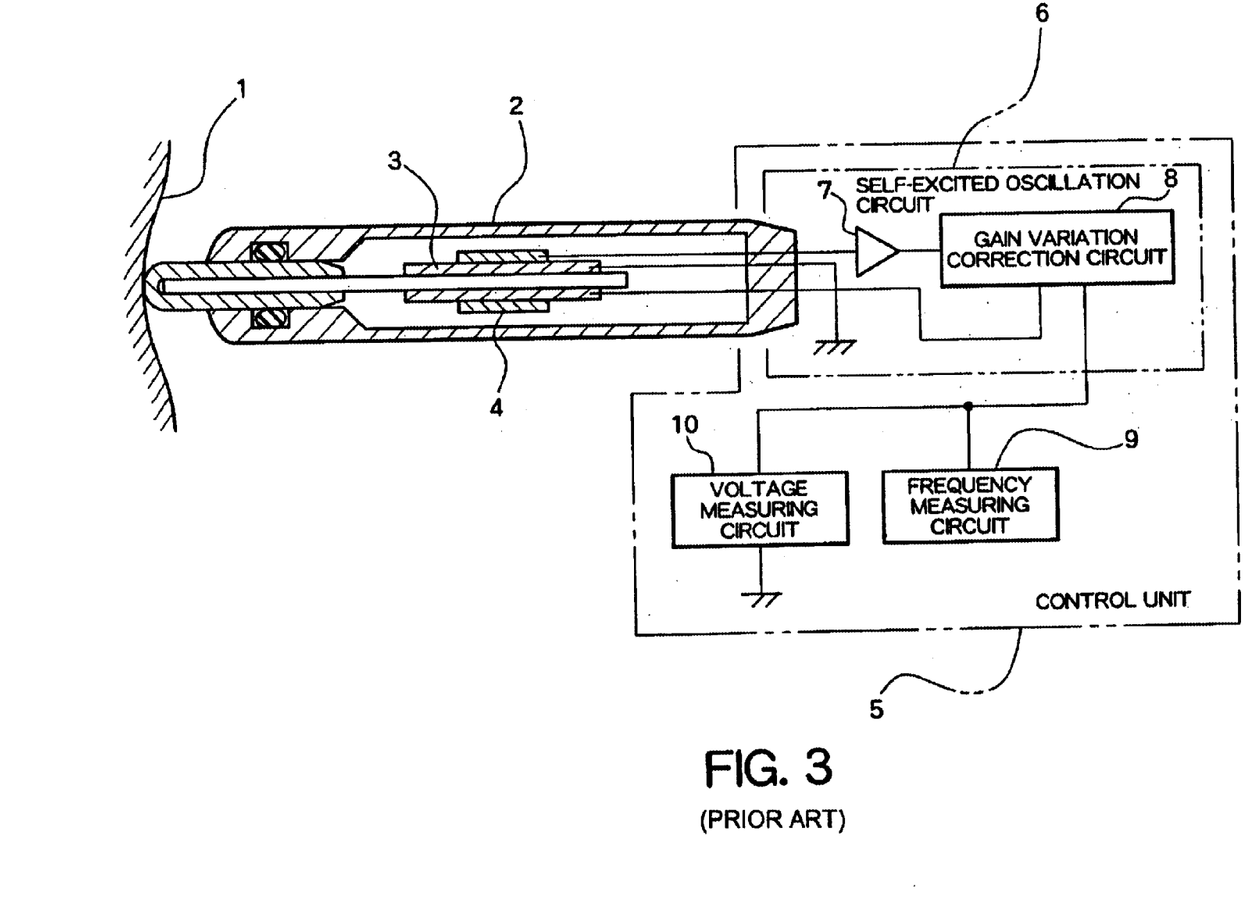
FIG. 3 illustrates a block diagram of an apparatus for measuring hardness in a conventional example.

One conventional method for measuring the hardness of a tissue material of a living body is a method that presses a probe against the material to be measured, applies vibration thereto, detects mechanical/electrical response of the tissue material of the living body to the input vibration using a sensor and obtains characteristic values corresponding to the hardness based on variation in the frequency and phase, etc. Examples of this method are disclosed in, for example, "Measurements of the Hardness of a Soft Material with a Piezoelectric Vibrometer and Their Analysis" (Sadao Omata, Medical Electronics and Bioengineering, Vol. 28, No. 1, 1990, pp 1–8) and "New tactile sensor like the human hand and its applications" (S. Omata et al, Sensors and Actuators A, 35 (1992) pp9–15). FIG. 3 shows an apparatus for measuring the hardness of tissue of a living body disclosed in Japanese Patent Laid-Open Publication No. Hei 9-145691 as a conventional example. FIG. 3 shows a probe unit 2 pressed against the material 1 to be measured of the living body, for example, a tissue of the skin, or a tissue of viscus, such as liver tissue. The probe unit 2 includes a vibrator 3 and a strain detection sensor 4, and is connected to an external control unit 5. The control unit 5 has a self-excited oscillation circuit 6 and the self-excited oscillation circuit 6 has an amplifier 7 and a gain variation correction circuit 8. Furthermore, the self-excited oscillation circuit 6 is connected to a frequency measuring circuit 9 to measure its frequency and a voltage measuring circuit 10 to measure its amplitude.

The operation of this conventional example will be explained below. When the probe unit 2 is pressed against the material 1, the vibrator 3 inside the probe unit 2 generates self-excited oscillated vibration as an electric signal is converted to mechanical vibration by a mechanical/electrical vibration system of the vibrator 3 and the self-excited oscillation circuit 6 in the control unit 5, and the vibration is input from the end of the probe unit 2 to the material 1. The material 1 responds to this input vibration, according to its mechanical vibration transmission characteristics. The strain detection sensor 4 detects this output vibration (strain) and converts it to an electric signal. The vibrator 3 and the strain detection sensor 4 can be implemented by, for example, a piezoelectric vibration element and a piezoelectric sensor. The vibrator 3 and the strain detection sensor 4 together with the amplifier 7 form a feedback loop and then osculation is self-excited. Here, as a result of the material 1 responding to the input signal from the vibrator 3, generally the frequency changes, a phase difference is generated and the amplitude is reduced, but the gain variation correction circuit 8 has a function of correcting the amplitude gain of the output signal of the strain detection sensor 4. Furthermore, because the gain variation correction circuit 8 is formed in the feedback loop of the self-excited oscillation circuit 6, feedback is provided in such a way that the phase difference generated becomes to zero while the amplitude gain is being corrected. When the phase difference is fed back to zero, the resonance frequency of the mechanical/electrical vibration system, which includes the material 1, the vibrator 3, the self-excited oscillation circuit 6, and the strain detection sensor 4, can be obtained by the frequency measuring circuit 9.

Figure 4:
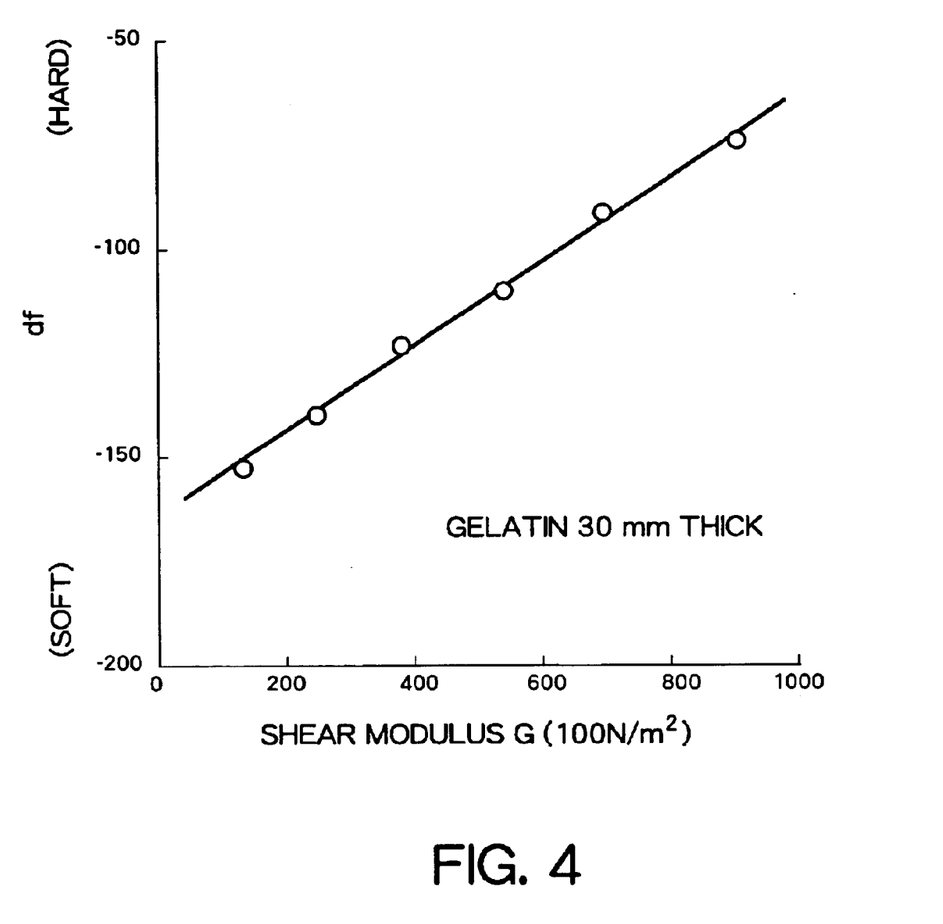
FIG. 4 illustrates a relationship between frequency variation df and the shear modulus G.
Figure 5:
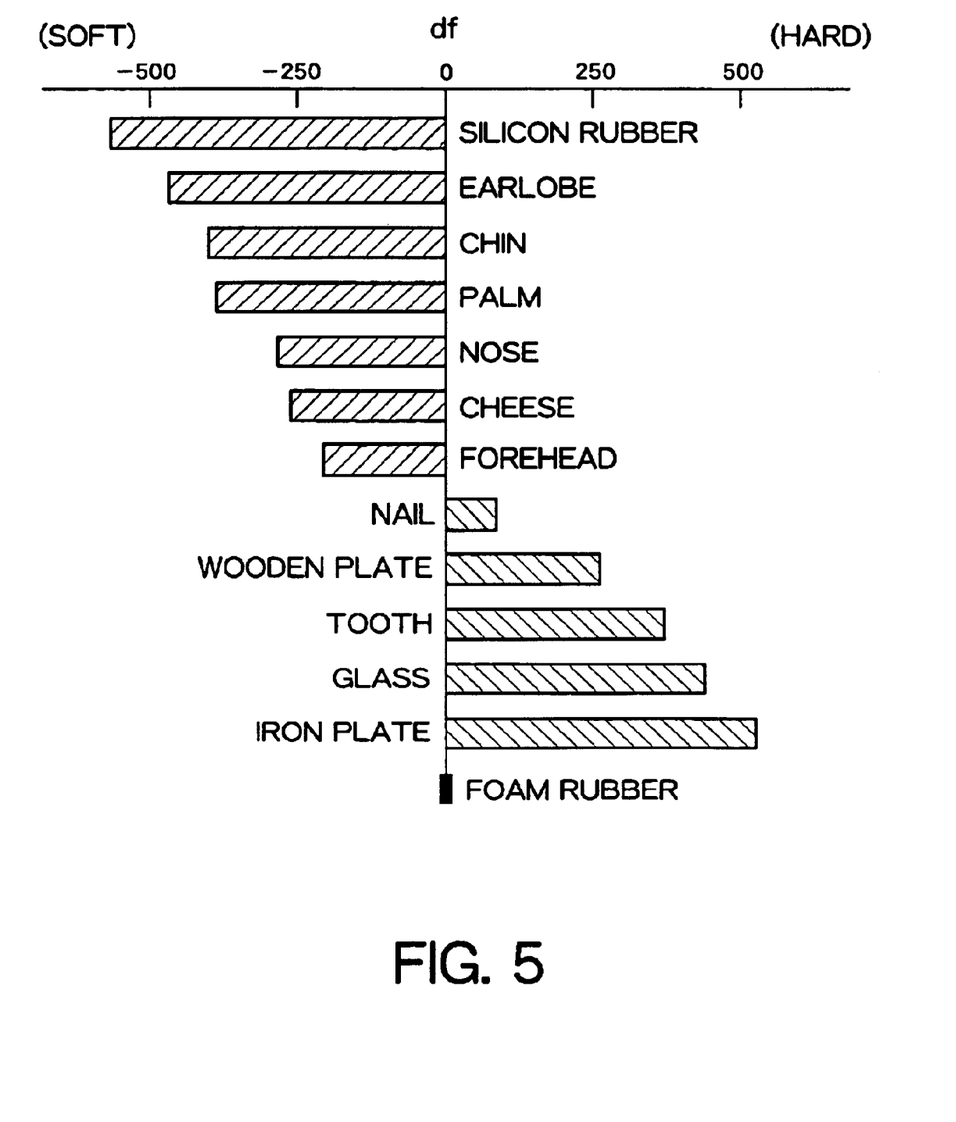
FIG. 5 illustrates frequency variation df of various materials using a foam rubber as a reference.

As is well known, because this resonance state is a speed resonance state, the resonance amplitude reaches its maximum value when the phase is zero, irrespective of the damping constant of the system; this is unlike a displacement resonance state or an acceleration resonance state. Therefore, as irrespective of the damping constant, it is possible to calculate a spring constant of the system by obtaining the resonance frequency when the phase is zero. Therefore, a frequency variation df between this resonance frequency and the frequency when the probe unit 2 is not in contact with the material 1 is the characteristic value corresponding to the hardness of the material 1, that is, the spring constant of the material. For example, FIG. 4 shows a relationship between the frequency variation df and the shear modulus measured by another method in the case of a gelatin of 30 mm in thickness. FIG. 5 shows values of frequency variation df of various materials containing tissues of the living body using foam rubber as a reference. From the frequency variation df in measured in this manner, it is possible to calculate the hardness of the material 1 based on the correspondence with the shear modulus G, the correspondence with the Young's modulus using a known relational expression, and the correspondence with a spring constant of the material 1 against which a specimen having a certain diameter is pressed.

Then, a CT value of a tissue of a living body obtained using an X-ray CT scanner will be explained. The X-ray CT scanner is an apparatus that scans an object such as the tissue of the living body while irradiating the object with X-rays from an X-ray tube and relatively moving with respect to the object, measures the amount of X-rays that have passed through the object using a detector such as a Xe gas ion chamber system and obtains a position, a shape and a size of an organ inside the object using three-dimensional image processing. The basic principle of this measurement is based on the characteristic that attenuation of X-rays passing through a material varies depending on the material, that is, photons introduced into the tissue of the living body measured show a specific attenuation under the influence of the interaction with atoms of the material making up the tissue of the living body, that is, the interaction such as the photo-electric effect and Compton effect, etc. For an X-ray characteristics expression of an organ, etc., an X-ray absorption value of the material generally converts to a numerical value relative to the value of water which is considered to be zero, and this value is used as a CT value. Therefore, the CT value is represented in the following expression (1):

$$CT\ value=\{(\text{an attenuation factor of various materials})/(\text{an attenuation factor of water})\}-1 \quad (1)$$

Figure 6:
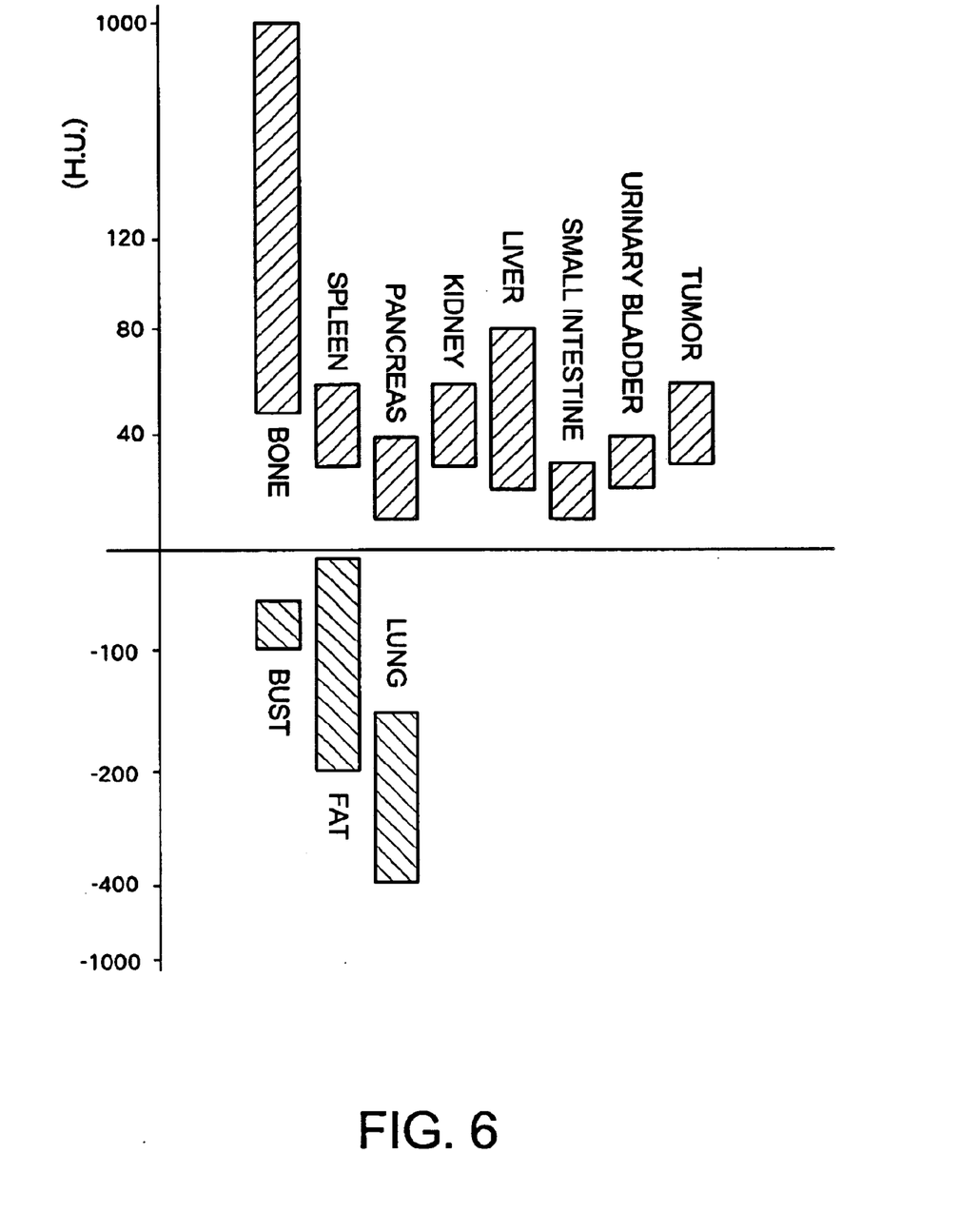
FIG. 6 is an example of reported CT values of various human body tissues.

The unit of the CT value is expressed in Hounsfield unit (H.U.). FIG. 6 shows an example of reported CT values of various tissues of the human body. The CT value of the bone is determined by its inorganic component, and CT values of other organs are determined by components such as protein, water, and fat. That is, over an entire wide area irradiated with X-rays, the X-ray CT scanner can obtain information with high spatial resolution of the detector, not only such as the position, the size, and the shape of the tissue in the living body, but also such as X-ray absorption characteristics of the tissue of the living body from CT values, and variation of the tissue of the living body from CT value variation.

The apparatus for measuring hardness in the above-described conventional example can detect frequency variation which is characteristic values corresponding to the hardness through the function of the gain variation correction circuit as sufficiently large magnitude, and can thereby measure the hardness with fewer errors from a soft tissue to a hard tissue of the living body using a single apparatus. However, because such measurement is performed with the probe unit pressed against the material to be measured, the hardness is obtained as an average value of the area measured. Therefore, when the measurement is performed using a large probe, there is a limit of the spatial resolution such as positions. However, when the measurement is performed using a small probe, it is necessary to repeatedly change positions from one place to another to obtain data of a wide area. For example, when there a hardened area of extremely small size is present in an organ being scanned, it is difficult to specify the micro area from the wide area using a large probe, while it will take a considerable amount of time for a small probe to find the area. This problem hampers configuration of an apparatus for measuring the hardness of the tissue of the living body with high spatial resolution over a wide area.

On the other hand, the CT value obtained from the X-ray CT scanner has high resolution in three-dimensional space. However, the CT value expresses the X-ray absorption characteristic relative to water and the CT value alone cannot express flexibility and rigidity such as the hardness of a material, and it is therefore not possible to express the correspondence with the hardness of abnormalities of tissue of a living body, such as those found by palpation.

The present invention advantageously solves the above-described problems of the conventional technology and make it possible to measure the hardness of a material having high spatial resolution over a wide area, especially the hardness of tissue of a living body, such as organ tissue, and to further measure the hardness of a micro area of the entire organ. The present invention also advantageously provides an apparatus for measuring the hardness of the material capable of expressing flexibility and rigidity of the tissue of the living body from the CT value of the X-ray CT scanner. The present invention still further advantageously provides a recording medium capable of outputting the hardness data of such a material using a computer.

DISCLOSURE OF INVENTION

Figure 1:
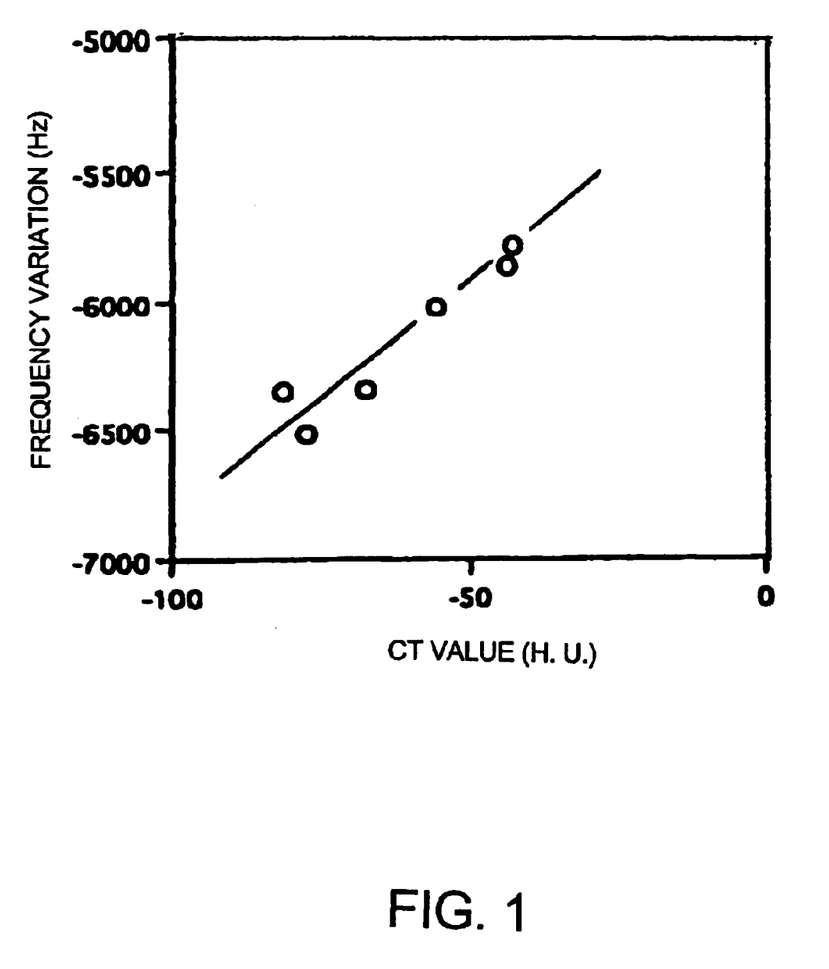
FIG. 1 shows a correlation between the CT value and the frequency variation indicating the hardness of a material.

The present invention is based on the finding that there is a certain correlation between the hardness of a material and the material's X-ray absorption value. For example, FIG. 1 shows a relationship between the CT value and the frequency variation indicating the hardness of a material in the case of fat of a pig. FIG. 1 is a graph showing a correlation between the frequency variation as an indicator of the hardness of the material on the vertical axis and the CT value of the same material on the horizontal axis. The frequency variation is obtained by pressing a probe against the material, vibrating the material, and detecting a mechanical vibration response to the input vibration using a sensor, and the frequency variation is the frequency difference between the input signal and the output signal. The CT value is determined using a commercially available X-ray CT measuring instrument. From FIG. 1, the certain clear correlation is observed between the hardness of the material and X-ray absorption values such as CT values.

Based on that property, it was realized that that the advantages supplied by the present invention can be achieved by an apparatus for measuring hardness of a material comprising inputting means for inputting an X-ray absorption value of a measured material, correspondence storing means for storing the correspondence relationship between X-ray absorption value data and hardness data of a plurality of reference materials, operating means for performing operations for converting the input X-ray absorption value of the material to be measured to the hardness of the material to be measured using the correspondence relationship, and outputting means for outputting the converted hardness of the material to be measured.

In such a configuration, converting the X-ray absorption value of the material in a micro area to the hardness of the material makes it possible to measure the hardness of the micro area. Furthermore, it is possible to convert an X-ray absorption value to the hardness of the material, a high utility value.

The apparatus for measuring hardness of tissue of a living body according to the present invention may include X-ray absorption value measuring means for scanning and irradiating the tissue of the living body to be measured with X-rays and measuring an X-ray absorption value of the tissue of the living body to be measured, a correspondence storage apparatus for storing the correspondence relationship between the X-ray absorption value data and the hardness data of a plurality of reference portions of tissue of the living body, a hardness conversion operating apparatus for performing operations for converting the X-ray absorption value to the hardness of the tissue of the living body and a display that outputs the converted hardness of the tissue of the living body to be measured.

When such a configuration is employed, the tissue of the living body to be measured is scanned and irradiated with X-rays and the measured X-ray absorption value is converted to the hardness of the tissue of the living body to be measured. Because the X-ray absorption value obtained by the X-ray absorption value measuring means has high spatial resolution over a wide area, it is possible to obtain and output the hardness of even a micro area, and to measure the hardness over a wide area with high spatial resolution. It is also possible to convert the X-ray absorption value to the hardness of a material expressing flexibility and rigidity.

The outputting means preferably outputs a two-dimensional hardness distribution of the tissue of the living body.

The X-ray absorption value is preferably the CT value, when the CT value is defined as the X-ray absorption value of the material represented in a numerical value relative to water whose CT value is considered to be zero.

Furthermore, the recording medium according to the present invention records the correspondence relationship between the CT value data and the hardness data of a plurality of reference materials and, by using a computer, the recording medium is capable of inputting the CT value data of the material to be measured and outputting the hardness of the material to be measured.

When an input signal is provided from a vibrator to the material to be measured and an output signal is obtained from the material to be measured, the hardness data is preferably the data obtained from a frequency variation between the input signal and output signal.

BEST MODE FOR CARRYING OUT THE INVENTION

Figure 2:
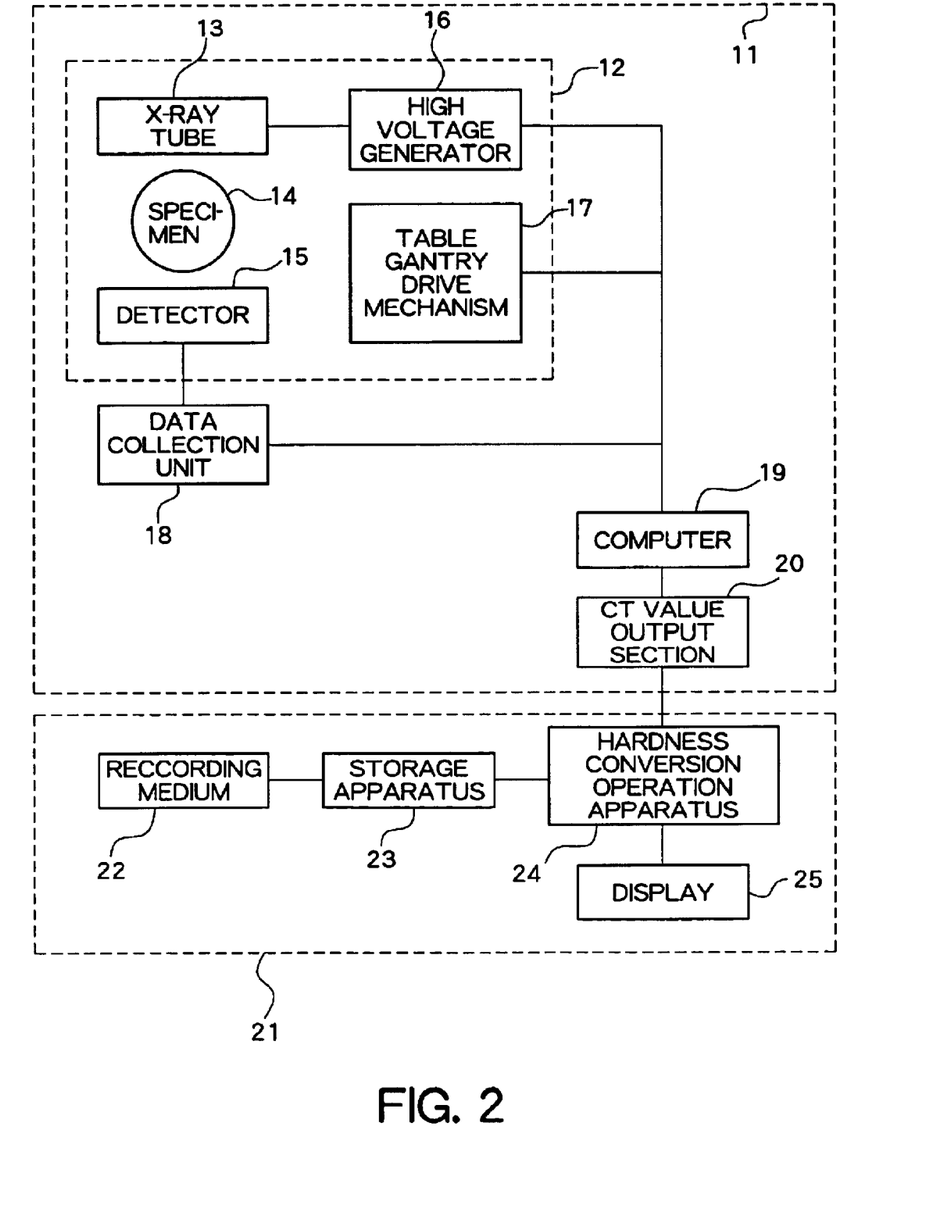
FIG. 2 is a block diagram of an apparatus for measuring the hardness of a material according to an embodiment of the present invention.

With reference now to the attached drawings, a preferred embodiment of the present invention will be explained in detail below. FIG. 2 shows an apparatus for measuring the hardness of a tissue of a living body according to the present invention. This apparatus includes X-ray absorption value measuring means 11 and a hardness conversion section 21. The X-ray absorption value measuring means 11 includes an X-ray scanning section 12 and the interior thereof is designed to allow a specimen 14, such as the tissue of the living body, to be placed facing an X-ray tube 13 and a detector 15 such as a Xe gas ion chamber system is placed behind the specimen 14 from the sight of the X-ray tube 13. A high-voltage generator 16 is connected to the X-ray tube 13 and a table gantry drive mechanism 17 is connected with the X-ray tube 13, the specimen 14 and the detector 15. A data collection unit 18 is connected to the detector 15 and a computer 19 is connected to the high-voltage generator 16, the table gantry drive mechanism 17, and the data collection unit 18. The computer 19 is connected to a CT value output section 20.

This X-ray absorption value measuring means 11 is connected to a hardness conversion section 21 and the hardness conversion section 21 is provided with a hardness conversion operation apparatus 24 which is in turn connected to all of a storage apparatus 23 employing a recording medium 22, the CT value output section 20, and a display 25.

The operation of the apparatus for measuring the hardness of living body tissue configured as described will be explained below. In the X-ray absorption value measuring means 11, a high voltage is supplied to the X-ray tube 13 from the high-voltage generator 16 to excite X-rays, the specimen 14, such as a tissue of a living body, is scanned with X-ray beams, the detector 15 detects the intensity of the X-rays passing through the specimen 14, and converts the detected intensity to an electrical signal, which is then collected by the data collection unit 18. By use of the table gantry drive mechanism 17, the X-ray tube 13 is moved relative to the specimen 14 and the detector 15 so that the specimen 14 is scanned with X-ray beams three-dimensionally over a wide area. Therefore, the data collection unit 18 collects the data of the intensity of the X-rays that have passed through the specimen 14 such as the tissue of the living body with high spatial resolution of the detector 15 over the wide area of the specimen 14 irradiated with X-rays. The mechanism of these components are controlled by the computer 19. Furthermore, the computer 19 determines the position, shape, and size of the organ inside the specimen 14 by using three-dimensional image processing based on the data of the detected intensity of the X-rays passing through the specimen 14, such as the tissue of the living body, as collected by the data collection unit 18 and on the control condition data of the component mechanisms. According to these data, the X-ray absorption value corresponding to the specific position of the specimen 14 is obtained, and then the CT value generally used as the X-ray absorption value is calculated using above-described expression (1). Thus, the specific position information of the specimen 14 and the corresponding CT value are output to the CT value output section 20.

A so-called X-ray CT scanner may be employed as the X-ray absorption value measuring means 11. When a general use X-ray CT scanner is not provided with the CT value output section 20, it is possible to provide a special CT value calculation apparatus or provide the computer 19 with the function of the CT value output section 20.

At the hardness conversion section 21, the recording medium 22 is inserted in the storage apparatus 23. The recording medium 22 stores the correspondence relationship between the CT value data and the hardness data of a plurality of reference materials and is capable of inputting the CT value data of the material and outputting the hardness data of the material using the computer. The storage apparatus 23 reads out, and temporarily store, the correspondence relationship.

The correspondence relationship between the CT value data and the hardness data of a plurality of reference portions of tissue of the living body can be obtained by performing measurements for obtaining the CT value and the hardness for the same material, and performing correlation-related processing. This correspondence relationship can be given in the forms of a correspondence expression of a calibration curve, or the forms of a table showing a one-to-one correspondence between the CT value data and the hardness data, or the forms of a program.

Then, the CT value corresponding to the specific position of the specimen 14 output from the CT value output section 20 is input to the hardness conversion operation apparatus 24. The hardness conversion operation apparatus 24 reads out the temporarily stored correspondence relationship from the storage apparatus 23, and performs a conversion operation or a search on the correspondence relationship with the input CT value of the specific position of the specimen 14. Thus, the CT value is converted to the hardness data. The hardness conversion operation apparatus 24 outputs this hardness data and the corresponding position information on the display 25 as, for example, printer image data, or display data by a liquid crystal display device or CRT.

The above-described embodiment has described the case where a so-called X-ray CT scanner is used, but if the sample shape of the specimen 14 is unified to a certain standard shape (standard thickness, etc.), the present invention can be implemented by using a detector such as a Xe gas ion chamber system of measuring the X-ray absorption value of the standard shape sample.

Furthermore, the above-described embodiment has described the case where a single-piece structure of the X-ray absorption value measuring means 11 and the hardness conversion section 21 is used, but the present invention can be implemented as a combination of an X-ray absorption value measuring equipment (11) and a hardness conversion equipment (21) The hardness conversion equipment (21) can be implemented by including inputting means for inputting the CT value of the specimen 14, the recording medium 22, the storage apparatus 23, the hardness conversion operation apparatus 24 and the display 25 as outputting means. In this case, the hardness conversion equipment (21) of the present invention can also be implemented by a commercially available computer. The hardness conversion computer has the appropriate performance capable of running the program to input the CT value data of the specimen 14 and output the hardness data of the specimen 14 using the recording medium 22 that records the correspondence relationship between the CT value data and the hardness data of a plurality of reference materials.

Furthermore, the above-described embodiment has described the case where the recording medium 22 is used, but the present invention can be implemented by storing a relational expression or a table specifying the correspondence relationship between the CT value data and the hardness data of a plurality of reference materials in the storage apparatus 23.

INDUSTRIAL APPLICABILITY

The present invention is applicable to an apparatus for measuring the hardness of a material, an apparatus for measuring the hardness of a tissue of a living body, and a recording medium capable of outputting the hardness data concerning a material.

What is claimed is:

1. An apparatus for measuring hardness of a material, comprising:

inputting means for inputting a measured X-ray absorption value for a material to be measured;

correspondence storing means for storing a correspondence relationship between X-ray absorption value data and hardness data of a plurality of reference materials;

operating means for performing operations for converting the input X-ray absorption value of the material to be measured to the hardness of the material to be measured using the correspondence relationship; and outputting means for outputting the converted hardness of the material to be measured, wherein the hardness data is hardness data obtained from a frequency variation between a non-contact-frequency when a hardness measuring probe is not in contact with the material to be measured, and a contact-frequency when the probe is pressed against the material to be measured, a probe and a self-excited oscillation circuit connected to the probe forming a feedback loop for causing self-excited oscillation, and the contact-frequency is a frequency when a phase difference is reduced to zero by a correction circuit provided in the feedback loop, the phase difference being generated as a result of the material responding to the input vibration provided to the material to be measured from a vibrator in the probe.

2. The apparatus for measuring hardness of a material according to claim 1, wherein the X-ray absorption value is a CT value defined as the X-ray absorption value of the material represented in a numerical value relative to water whose CT value is considered to be zero.

3. An apparatus for measuring hardness of tissue of a living body, comprising:

X-ray absorption value measuring means for scanning and irradiating the tissue of the living body to be measured with X-rays and measuring an X-ray absorption value of the tissue of the living body to be measured;

a correspondence storage apparatus for storing a correspondence relationship between X-ray absorption value data and hardness data of a plurality of reference portions of tissue of the living body;

a hardness conversion operation apparatus for performing operations for converting the X-ray absorption value to the hardness of the tissue of the living body to be measured using the correspondence relationship; and a display that outputs the converted hardness of the tissue of the living body to be measured, wherein the hardness data is hardness data obtained from a frequency variation between a non-contact-frequency when a hardness measuring probe is not in contact with the material to be measured, and a contact-frequency when the probe is pressed against the material to be measured, a probe and a self-excited oscillation circuit connected to the probe forming a feedback loop for causing self-excited oscillation, and the contact-frequency is a frequency when a phase difference is reduced to zero by a correction circuit provided in the feedback loop, the phase difference being generated as a result of the material responding to the input vibration provided to the material to be measured from a vibrator in the probe.

4. The apparatus for measuring hardness of tissue of a living body according to claim 3, wherein the X-ray absorption value is a CT value defined as the X-ray absorption value of the material represented in a numerical value relative to water whose CT value is considered to be zero.

5. The apparatus for measuring hardness of tissue of a living body according to claim 3, wherein the display outputs a two-dimensional hardness distribution of the tissue of the living body.

6. The apparatus for measuring hardness of tissue of a living body according to claim 5, wherein the X-ray absorption value is a CT value defined as the X-ray absorption value of the material represented in a numerical value relative to water whose CT value is considered to be zero.

7. A machine-readable medium that records a correspondence relationship between CT value data and hardness data of a plurality of reference materials, and is capable of inputting the CT value of the material to be measured and outputting the hardness of the material to be measured using a computer;

wherein the hardness data is hardness data obtained from a frequency variation between a non-contact-frequency when a hardness measuring probe is not in contact with the material to be measured, and a contact-frequency when the probe is pressed against the material to be measured, a probe and a self-excited oscillation circuit connected to the probe forming a feedback loop for causing self-excited oscillation, and the contact-frequency is a frequency when a phase difference is reduced to zero by a correction circuit provided in the feedback loop, the phase difference being generated as a result of the material responding to the input vibration provided to the material to be measured from a vibrator in the probe.

* * * * *